United States Patent [19]

Kolts et al.

[11] Patent Number: 5,157,188
[45] Date of Patent: Oct. 20, 1992

[54] METHANE CONVERSION

[75] Inventors: John H. Kolts, Ochelata; James B. Kimble, Bartlesville, both of Okla.

[73] Assignees: Phillips Petroleum Company, Bartlesville, Okla.; Atlantic Richfield Company, Los Angeles, Calif.

[21] Appl. No.: 713,652

[22] Filed: Mar. 19, 1985

[51] Int. Cl.$^5$ .............................................. C07C 2/00
[52] U.S. Cl. ..................... 585/500; 585/415; 585/417; 585/418; 585/541; 585/654; 585/656; 585/658; 585/661; 585/741; 585/943
[58] Field of Search ............... 585/415, 417, 418, 500, 585/541, 654, 656, 658, 661, 741, 943

[56] References Cited

U.S. PATENT DOCUMENTS

| | | | |
|---|---|---|---|
| 1,801,382 | 4/1931 | Wietzel | 585/943 |
| 1,863,212 | 6/1932 | Winkler | 585/415 |
| 1,987,092 | 1/1935 | Winkler | 585/417 |
| 2,123,799 | 7/1938 | Peabelnick | 585/417 |
| 2,396,697 | 3/1946 | Gorin | 585/415 |
| 2,467,551 | 4/1946 | Gorin | 585/943 |
| 4,239,658 | 12/1980 | Mitchell, III et al. | 585/417 |
| 4,497,970 | 2/1985 | Young | 585/415 |
| 4,513,164 | 4/1985 | Olah | 585/943 |
| 4,523,049 | 6/1985 | Jones et al. | 585/500 |
| 4,523,050 | 6/1985 | Jones et al. | 585/943 |

FOREIGN PATENT DOCUMENTS 3237079 4/1984 Fed. Rep. of Germany ...... 585/500

OTHER PUBLICATIONS

Symposium on the New Surface Science in Catalysis, Presented Before the Division of Colloid and Surface Chem. and the Division of Petroleum Chemistry, Inc., Philadelphia Meeting, "Evidence for the Formation of Gas Phase Radicals at Surfaces", Aug., 1984.

Primary Examiner—Patrick P. Garvin
Assistant Examiner—E. D. Irzinski
Attorney, Agent, or Firm—K. K. Brandes

[57] ABSTRACT

A method for the oxidative conversion of methane, to higher hydrocarbons, particularly ethylene and ethane, in which a methane-containing gas, such as natural gas, and a free oxygen containing gas are contacted with a contact material selected from the group consisting of:
(a) a component comprising: (1) at least one oxide of a metal selected from the group consisting of calcium, strontium and barium and, optionally, a component comprising: (2) at least one material selected from the group consisting of chloride ions, compounds containing chloride ions, tin and compounds containing tin;
(b) a component comprising: (1) at least one metal selected from the group consisting of sodium, potassium and compounds containing said metals, a component comprising: (2) at least one metal selected from the group consisting of Group IIA metals and compounds containing said metals, and, optionally, a component comprising: (3) at least one material selected from the group consisting of chloride ions, compounds containing chloride ions, tin and compounds containing tin; and
(c) a component comprising: (1) at least one metal selected from the group consisting of Group IA metals and compounds containing said metals, a component comprising: (2) at least one metal selected from the group consisting of calcium, strontium, barium and compounds containing said metals and, optionally, a component comprising: (3) at least one material selected from the group consisting of chloride ions, compounds containing chloride ions, tin and compounds containing tin.

32 Claims, No Drawings

METHANE CONVERSION

The present invention relates to methane conversion. In a more specific aspect, the present invention relates to methane conversion t higher hydrocarbons. In a still more specific aspect, the present invention relates to methane conversion to ethylene and ethane.

BACKGROUND OF THE INVENTION

Olefins, such as ethylene and propylene have become major feedstocks in the organic chemical and petrochemical industries. Of these, ethylene is by far the more important chemical feedstock, since the requirements for ethylene feedstocks are about double those for propylene feedstocks. Consequently, feedstocks for the production of ethylene are in relatively short supply.

Numerous suggestions have been made for the production of ehtylene from various feedstocks by a variety of processes.

At the present time, ethylene is produced almost exclusively by dehydrogenation or pyrolysis of ethane and propane, naptha and, in some instances, gas oils. About 75% of the ethylene is produced by steam cracking of ethane and propane derived from natural gas. However, natural gas contains as little as 5 volume percent and, in rare instances, as much as 60 volume percent of hydrocarbons other than methane, the majority of which is ethane. However, typical natural gases contain less than about 12 to 15% of ethane. In addition to the relatively small quantities of ethane and propane available for use, separation of these components from natural gas is itself an expensive and complex process, usually involving compression and expansion, cryogenic techniques and combinations thereof.

It would, therefore, be highly desirable to be able to produce ethylene from the much more abundant methane. However, methane's high molecular stability, compared to other aliphatics, makes its use in ethylene production difficult and no significant amount of ethylene is produced commercially from methane at the present time.

Pyrolytic or dehydrogenative conversion of methane or natural gas to higher hydrocarbons has been proposed. However, relatively severe conditions, particularly temperatures in excess of 1000° C., are required. In addition, such reactions are highly endothermic and thus energy intensive. In order to reduce the severity of the conditions, particularly temperature, numerous proposals to catalyze pyrolytic reactions have been made. Some of these processes do, in fact, reduce the required temperatures, but the conversion of methane and the selectivity to ethylene are still quite low.

Another promising approach is the oxidative conversion of methane or natural gas to higher hydrocarbons. However, these techniques are still in the developmental stage and experimentation is hampered by differences of opinion and lack of a complete understanding of the process. For example, most workers in the art refer to the process as "oxidative coupling". However, there is little agreement with regard to the function performed by the oxygen and how this function is performed. Accordingly, the terminology, "oxidative coupling", will be avoided herein, and the present process, irrespective of the function of the oxygen or of the manner in which it performs its function, will be referred to as "oxidative conversion of methane". In such processes, it is conventional to contact the methane with solid materials. The nature of these contact materials, the function thereof and the manner in which such function is performed are also subject to diverse theories. For example, workers in the art refer to the function of the contact material as a purely physical phenomenon, in some cases as adsorption-desorption, either of atomic or molecular oxygen and either on the surface or occluded within the solid material, oxidation-reduction utilizing multivalent metals capable of oxidation-reduction, adsorption and desorption of the hydrocarbons on the solid materials, a free radical mechanism, etc. Consequently, the solid materials, utilized in the process, are referred to as "contact materials", "promoters", "activators" and "catalysts". Accordingly, in order to avoid functional categorization, the terms "solid contact material" or "solid contact materials" will be utilized in the present application.

Based on the prior art, oxidative conversion of methane results in the formation of a variety of products. The most readily produced products are carbon dioxide, carbon monoxide and/or water and methanol, formaldehyde and other oxygenated hydrocarbons in combination with one or more of carbon dioxide, carbon monoxide and water. Higher hydrocarbons, particularly ethylene and ethane, are either not formed or are formed in such small quantities that commercially viable processes have not been developed to data. Along with poor selectivity to higher hydrocarbons, particularly ethylene and ethane and still more particularly to ethylene, such processes also result in low conversions of the methane feed.

It is clear from the above that the suitability of particular contact materials is unpredictable. In addition to being dependent upon the type of contact material, the conversion of methane and selectivity to particular products also depends upon the conditions and the manner in which the reaction is carried out, and there is also little basis for predicting what conditions or what mode of operation will result in high conversions and selectivity to particular products.

SUMMARY OF THE INVENTION

It is therefore, an object of the present invention to provide an improved method for the conversion of methane. Another and further object is to provide an improved method for the oxidative conversion of methane. Yet another object is to provide a method for the oxidative conversion of methane at improved conversion levels. Another and further object of the present invention is to provide a method for the oxidative conversion of methane wherein improved selectivity to higher hydrocarbons is attained. A further object of the present invention is to provide a method for the oxidative conversion of methane which results in improved conversion and selectivity to higher hydrocarbons. A still further object of the present invention is to provide a method for the oxidative conversion of methane which results in improved selectivity to ethylene and ethane. Yet another object of the present invention is to provide a method for the oxidative conversion of methane which results in improved conversion and selectivity to ethylene and ethane. Another object of the present invention is to provide a method for the oxidative conversion of methane which results in improved selectivity to ethylene. Another and further object of the present invention is to provide a method for the oxidative conversion of methane which results in improved conversion and selectivity to ethylene. A still further object of the present invention is to provide a method for the oxidative conversion of methane which can be carried out in a simple, continuous manner. A further object of the present invention is to provide a method for the oxidative conversion of methane which can be carried out utilizing inexpensive starting materials. Another object of the present invention is to provide a method for the oxidative conversion of methane which can be carried out under relatively mild conditions. A still further object of the present invention is to provide a method for the oxidative conversion of methane utilizing an improved contact material.

These and other objects and advantages of the present invention will be apparent from the following description.

In accordance with the present invention, it has been found that methane can be converted to higher hydrocarbons, particularly ethylene and ethane, by contacting a methane-containing gas and a free oxygen containing gas with a contact material selected from the group consisting of:

(a) a component comprising: (1) at least one oxide of a metal selected from the group consisting of calcium, strontium and barium and, optionally, a component comprising: (2) at least one material selected from the group consisting of chloride ions, compounds containing chloride ions, tin and compounds containing tin;

(b) a component comprising: (1) at least one metal selected from the group consisting of sodium, potassium and compounds containing said metals, a component comprising: (2) at least one metal selected from the group consisting of Group IIA metals and compounds containing said metals; and, optionally, a component comprising: (3) at least one material selected from the group consisting of chloride ions, compounds containing chloride ions, tin and compounds containing tin; and (c) a component comprising: (1) at least one metal selected from the group consisting of Group IA metals and compounds containing said metals, a component comprising: (2) at least one metal selected from the group consisting of calcium, strontium, barium and compounds containing said metals and, optionally, a component comprising: (3) at least one material selected from the group consisting of chloride ions, compounds containing chloride ions, tin and compounds containing tin under conditions sufficient to produce a significant amount of such higher hydrocarbons.

DETAILED DESCRIPTION OF THE INVENTION

In accordance with most previous theories of the function and operation of contact materials for the oxidative conversion of methane to higher hydrocarbons, particularly ethylene and ethane, the reaction has been carried out in the absence of an oxygen-containing gas, with the oxygen theoretically being supplied by the contact material. As a result, the most utilized modes of operation have included treating the contact material with a free oxygen containing gas, such as oxygen or air, for a period of time sufficient to produce a reducible oxide of a multivalent metal, thereafter, contacting methane with the reducible metal oxide and, thereafter, treating the reduced metal oxide with a free oxygen containing gas to "regenerate" the same. Similarly, certain contact materials are contacted with a free oxygen containing gas to cause adsorption of oxygen on the contact material, methane is, thereafter, contacted with the contact material containing adsorbed oxygen and, thereafter, the contact material is again treated with a free oxygen containing gas. In both instances, the contact material, after treatment with a free oxygen containing gas, is purged with an inert gas, such as nitrogen, to remove excess oxygen which has not reacted with or been adsorbed on the contact material. Consequently, several techniques have been followed, including, carrying out the contact with methane and the contact with a free oxygen containing gas in separate reaction chambers or sequentially passing a free oxygen containing gas, a purge gas and methane through the contact material in a single reaction vessel. The disadvantages of either of these procedures will be evident to one skilled in the art.

In contrast to these prior art techniques, the method of the present invention is carried out by contacting methane with a contact material in the presence of a free oxygen containing gas.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen containing gas may be any suitable oxygen containing gas, such as oxygen, oxygen-enriched air or air. The method of the present application has been effectively carried out utilizing air as a source of oxygen.

When utilized in the present invention, the term "diluent gas" is meant to include any gaseous material present in the methane-containing gas, the free oxygen containing gas or in the form of an added gas which is essentially inert with respect to the oxidative conversion of methane and, thus, does not significantly decrease the conversion of methane and/or the selectively to the production of higher hydrocarbons.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

It has further been found, in accordance with the present invention, that the oxidative conversion of methane, in the presence of free oxygen, to higher hydrocarbons can be substantially improved by contacting the mixture of methane and free oxygen containing gas with a contact material selected from the group consisting of:

(a) a component comprising: (1) at least one oxide of a metal selected from the group consisting of calcium, strontium and barium and, optionally, a component comprising: (2) at least one material selected from the group consisting of chloride ions, compounds containing chloride ions, tin and compounds containing tin;

(b) a component comprising: (1) at least one metal selected from the group consisting of sodium, potassium and compounds containing said metals, a component comprising: (2) at least one metal selected from the group consisting of Group IIA metals and compounds containing said metals; and, optionally, a component comprising: (3) at least one material selected from the group consisting of chloride ions, compounds containing chloride ions, tin and compounds containing tin; and (c) a component comprising: (1) at least one metal selected from the group consisting of Group IA metals and compounds containing said metals, a component comprising: (2) at least one metal selected from the group consisting of calcium, strontium, barium and compounds containing said metals and, optionally, a component comprising: (3) at least one material selected from the group consisting of chloride ions, compounds containing chloride ions, tin and compounds containing tin.

Where combinations of sodium, potassium or mixtures thereof and a Group IIA metals and mixtures thereof, combinations of a Group IA metal and mixtures thereof and calcium, strontium, barium and mixtures thereof, and optional tin and chloride are referred to herein, the Group IIA metal or calcium, strontium, or barium will be referred to as the "base metal", whereas the sodium, potassium, Group IA metal, tin or chloride will be referred to as the "promoter", strictly as a matter of convenience, based on the fact that the "promoter" is generally the minor component of the contact material. It is to be clearly understood that such designations are not utilized to define the function or operation of the material, since the functions of the contact materials are not fully understood. It is believed that both metal components are necessary and appear to be active in the conversion of methane to higher hydrocarbons. For example, while such designation would classify calcium as a base metal it has been found, in accordance with the present invention, that calcium alone is active in promoting the conversion of methane to higher hydrocarbons, as are strontium and barium, based on their similarity to calcium. It has also been found that the presence of chloride ions in the contact material has a beneficial effect in the oxidative conversion of methane to higher hydrocarbons. The chloride ion may be present as a part of a compound of either the promoter metal or the base metal or as part of a separate compound. It has further been found that the presence of tin or a tin compound in the contact material also has a beneficial effect in the oxidative conversion of methane to higher hydrocarbons. Both chloride ions and tin are still more beneficial. Accordingly, a convenient form of these ingredients is in the form of tin chloride deposited on the base metal or mixed therein.

The term, "effective amount" is used herein to identify the quantity of promoter metal which, when present in the contact material, results in a significant increase in the conversion of methane and/or the selectivity to higher hydrocarbons, particularly ethylene and ethane and more particularly to ethylene, compared with an inactive contact material, for example, quartz, which has been found to be ineffective in the conversion of methane. Accordingly, in accordance with the present invention, the promoter metal is present in the contact material in amounts of at least an effective amount of the promoter metal up to about 100 wt. percent. While some Group IA metals alone have been found to result in the conversion of methane to ethylene and ethane, the conversion and selectivity are too low to be significant. Preferably, the contact material contains from about 0.1 to about 50 wt. percent of the promoter metal, more preferably between about 0.1 and about 15 wt. percent and still more preferably between about 1 and about 10 wt. percent. Ideally, the promoter metal content is between about 2 wt. percent and about 7 wt. percent. These percentages are the weight percent of the elemental promoter metal based on the total weight of the compound or compounds containing the base metal plus the compound or compounds containing the promoter metal. This designation of weight percent of promoter metal, as indicated, is utilized throughout the present application. When chloride ions or compounds containing the same are present, amounts of at least an effective amount up to about 100 wt. percent and, usually between about 0.1 wt. percent and 5 wt. percent, expressed as elemental chlorine based on the total weight of the contact material, are used. Tin may be present, in the contact material, in amounts from at least an effective amount up to about 100 wt. percent, usually between about 0.5 wt. percent and about 20 wt. percent. The tin content is also expressed as the wt. percent of elemental tin based on the total weight of the contact material.

Substantially any compound or compounds of the promoter metal and the base metal may be utilized in the contact materials so long of none of such compounds are detrimental to the effectiveness of the oxidative conversion of methane to higher hydrocarbons. The promoter metal and the base metal are usually in the form of their oxides or carbonates prior to initiation of the oxidative conversion of methane. During the course of the reaction, the promoter metal and/or base metal are believed to be converted to carbonates. Accordingly, any promoter metal or base metal compound capable of conversion to its oxide or carbonate in the presence of the reaction media and/or products, particularly carbon dioxide, may be utilized as the preferred metal compounds. However, it is preferred that the promoter metal and the base metal be in their predominantly oxide form.

The contact materials can be prepared from any suitable starting compounds and by any suitable method known in the art for the preparation of such mixtures in a solid form. For example the promotor metal and/or base metal may be derived from metal carbonates, hydroxides, oxides, nitrates, octoates, chlorides, etc. Conventional methods include co-precipitation from an aqueous, an organic or combination solution-dispersions, impregnation, dry mixing, wet mixing or the like, alone or in various combinations. In general, any method can be used which provides contact materials containing the prescribed components in effective amounts. The contact material can be prepared by mixing the ingredients, for example, promoter metal carbonate and base metal hydroxide, in a blender with enough water to form a thick slurry. The slurry can then be dried, usually at a temperature sufficient to volatilize the water or other carrier, such as about 220°

F. to about 450° F., and/or, therafter, calcined, for example at about 700° F. to 1200° F., for from 1 to 24 hours. In a specific case, the material was dried overnight at about 300° C. and thereafter calcined for four hours at 775° C. Drying and/or calcining is preferably in the presence of a free oxygen containing gas.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

In the runs of the examples, the contact materials were prepared by aqueous slurrying, drying and calcination. The contact material was loaded in a quartz reactor having a thermocouple well centered in the contact material bed. The reactor was brought up to temperature under nitrogen or air and thereafter methane and air (or oxygen) flow was begun. The gas inlet system included electronic flow measurement, a three-zone furnace for heating reactant gases and the contact material and a downstream analysis system. The reactor effluent was snap sampled, at any desired time, and analyzed for all paraffins and olefins between $C_1$ and $C_4$ and $N_2$, $O_2$, CO and $CO_2$, by gas chromatography. All contact materials are referred to in terms of weight percent of the designated element, based on the total weight of contact material.

The variables and results of this series of tests are set forth in the Table below. Conversion is mole percent of methane converted. Selectivity and yields are based on mole percent of methane feed converted to a particular product. The $CH_4$ rate can be expressed as cc/min/cc of contact material. For example, when 70 cc/min of $CH_4$ was fed to a reactor containing 20 cc of catalyst the flow rate would be 3.5 cc/min of $CH_4$/cc of contact material. The volumetric ratio of $CH_4$ to oxygen is also parenthetically given in terms of cc/min of $CH_4$ per cc/min of other gases (air or $N_2$) present. The promoter metals of the contact materials were in their oxide form and, as previously indicated, the percent of promoter metal is the weight percent of elemental promoter metal or metals based on the total weight of the promoter metal compound or compounds and the base metal compound.

TABLE

| Run No. | Contact Material | Vol., cc $CH_4$/Air | Vol. of Con. Mat | Sample Time (min) | Temp. (°C.) | Conversion | Selectivity | | | | | | | Conversion To | | |
|---|---|---|---|---|---|---|---|---|---|---|---|---|---|---|---|---|
| | | | | | | | $C_2=$ | $C_2$ | $C_2$'s | $C_3=$ | $C_3$ | $CO_2$ | CO | $C_2=$ | $C_2$'s | HC's |
| 1 | MgO | 70/80 | 20 cc | 6 | 700 | 14.5 | 8.5 | 10.1 | 18.6 | — | — | 51.3 | 30.1 | 1.23 | 2.70 | 2.70 |
| | | | | 60 | 705 | 15.7 | 6.8 | 8.9 | 15.7 | 0.1 | — | 54.7 | 29.5 | 1.07 | 2.46 | 2.48 |
| 2 | Na(3%)/MgO | 70/80 | 20 cc | 5 | 710 | 20.2 | 29.5 | 22.9 | 52.4 | 2.7 | 0.9 | 41.3 | 2.6 | 5.96 | 10.52 | 11.31 |
| | | | | 45 | 716 | 20.2 | 31.2 | 22.5 | 53.7 | 2.9 | 0.9 | 39.5 | 3.0 | 6.30 | 10.85 | 11.62 |
| | | | | 80 | 716 | 19.1 | 33.2 | 23.8 | 57.0 | — | — | 39.7 | 3.2 | 6.34 | 10.89 | 10.89 |
| 3 | CaO | 70/80 | 20 cc | 5 | 715 | 9.9 | 20.3 | 33.9 | 54.2 | — | 4.4 | 39.9 | 1.4 | 2.01 | 5.37 | 5.50 |
| | | | | 40 | 714 | 9.1 | 21.4 | 36.7 | 58.1 | — | — | 37.6 | 4.3 | 1.95 | 5.29 | 5.29 |
| | | | | 75 | 714 | 9.0 | 22.7 | 36.6 | 59.3 | — | — | 38.3 | 2.4 | 2.04 | 5.34 | 5.34 |
| | | | | 135 | 715 | 9.9 | 21.3 | 31.7 | 53.0 | 0.8 | 1.3 | 40.5 | 4.4 | 2.11 | 5.25 | 5.45 |
| 4 | Li(3%)/CaO | 70/80 | 20 cc | 17 | 707 | 18.0 | 40.9 | 27.3 | 68.0 | 3.7 | — | 25.3 | 2.7 | 7.36 | 12.24 | 12.91 |
| | | | | 53 | 711 | 19.0 | 38.7 | 28.6 | 67.3 | 3.7 | 1.0 | 24.9 | 3.1 | 7.35 | 12.79 | 13.68 |
| | | | | 90 | 711 | 18.0 | 38.3 | 26.6 | 64.9 | 3.8 | 1.1 | 26.9 | 3.4 | 6.89 | 11.68 | 12.56 |
| | | | | 1050 | 710 | 17.3 | 36.0 | 25.8 | 61.8 | 3.2 | — | 29.9 | 5.1 | 6.23 | 10.69 | 11.25 |
| 5 | Na(3%)CaO | 70/80 | 20 cc | 70 | 731 | 18.9 | 26.1 | 29.2 | 65.3 | 3.4 | 2.0 | 27.3 | 1.9 | 6.82 | 12.34 | 13.36 |
| | | | | 120 | 709 | 15.7 | 35.3 | 35.0 | 70.3 | 2.9 | 2.2 | 24.6 | — | 5.54 | 11.04 | 11.84 |
| | | 50/100 | 20 cc | 5 | 717 | 21.7 | 36.0 | 25.8 | 61.8 | 2.8 | 1.6˙ | 31.8 | 1.9 | 7.81 | 13.41 | 14.37 |
| | | | | 40 | 719 | 21.8 | 38.4 | 28.2 | 66.6 | 2.8 | — | 28.4 | 2.2 | 8.37 | 14.52 | 15.13 |
| 6 | K(3%)CaO | 100/100 | 25 cc | 6 | 710 | 10.7 | 19.5 | 36.0 | 55.5 | 1.1 | 1.7 | 36.0 | 2.6 | 2.09 | 5.94 | 6.24 |
| | | | | 51 | 704 | 8.5 | 19.9 | 44.8 | 64.7 | — | — | 35.3 | — | 1.69 | 5.50 | 5.50 |
| | | | | 96 | 702 | 9.8 | 19.0 | 38.9 | 57.9 | 1.2 | 1.9 | 36.1 | 2.8 | 1.86 | 5.67 | 5.98 |
| | | | | 130 | 700 | 9.9 | 19.5 | 38.6 | 58.1 | — | — | 39.0 | 2.9 | 1.93 | 5.75 | 5.75 |
| 7 | Li(3%)/CaO | 70/80 ($CH_4/N_2$) | 20 cc | 40 | 703 | 0.28 | — | — | — | — | — | 100 | — | — | — | — |
| | | | | | 703 | 0.28 | — | — | — | — | — | 100 | — | — | — | — |
| | | | | | 702 | 0.06 | — | — | — | — | — | 99.99 | — | — | — | — |

TABLE -continued

| Run No. | Contact Material | Vol., cc CH₄/Air | Vol. of Con. Mat | Sample Time (min) | Temp. (°C.) | Conversion | Selectivity $C_2=$ | $C_2$ | $C_2$'s | $C_3=$ | $C_3$ | $CO_2$ | CO | Conversion To $C_2=$ | $C_2$'s | HC's |
|---|---|---|---|---|---|---|---|---|---|---|---|---|---|---|---|---|
| 8 | Quartz | 70/80 | 20 cc | 40 | 740 | 0.00 | — | — | — | — | — | — | — | — | — | — |

It has also been found that the production of $CO_2$ was high and, hence, the HC selectivity was low, if the concentration of $O_2$ in the initial feed stream is high. Accordingly, the HC selectivity can be increased and the $CO_2$ production concomittantly decreased by staged addition of the free oxygen containing gas to provide an effective portion of the total $O_2$ at a plurality of spaced points along a continuous contact material bed or between separate contact material beds.

While specific materials, conditions of operation, modes of operation and equipment have been referred to herein, it is to be recognized that these and other specific recitals are for illustrative purposes and to set forth the best mode only and are not to be considered limiting.

What is claimed is:

1. A method for the conversion of methane to higher hydrocarbons, comprising:
    contacting a methane-containing gas and a free oxygen-containing gas with a solid contact material selected from the group consisting of:
    (A) a solid contact material consisting essentially of: (1) at least one oxide of at least one metal selected from the group consisting of sodium and potassium and (2) at least one oxide of at least one metal selected from the group consisting of Group IIA metals;
    (B) a solid contact material consisting essentially of: (1) at least one oxide of at least one metal selected from the group consisting of calcium, strontium and barium and (2) at least one material selected from the group consisting of chloride ions and compounds containing chloride ions; and
    (C) a solid contact material consisting essentially of: (1) at least one oxide of at least one metal selected from the group consisting of sodium and potassium, (2) at least one oxide of at least one metal selected from the group consisting of Group IIA metals and (3) at least one material selected from the group consisting of chloride ions and compounds containing chloride ions,
    under conditions sufficient to convert said methane to a significant amount of higher hydrocarbons.

2. A method in accordance with claim 1 wherein the solid contact material consists essentially of (1) at least one oxide of at least one metal selected from the group consisting of sodium and potassium and (2) at least one oxide of at least one metal selected from the group consisting of Group IIA metals.

3. A method in accordance with claim 2 wherein the sodium and potassium are present in an amount between about 0.1 and 50 wt. %, expressed in terms of the metal based on the total weight of the contact material.

4. A method in accordance with claim 1 wherein the solid contact material consists essentially of: (1) at least one oxide of at least one metal selected from the group consisting of calcium, strontium and barium and (2) at least one material selected from the group consisting of chloride ions and compounds containing chloride ions.

5. A method in accordance with claim 4 wherein the chloride ions are present in an amount between about 0.5 and 20 wt. %, expressed in terms of chlorine based on the total weight of the contact material.

6. A method in accordance with claim 1 wherein the solid contact material consists essentially of: (1) at least one oxide of at least one metal selected from the group consisting of sodium and potassium, (2) at least one oxide of at least one metal selected from the group consisting of Group IIA metals and (3) at least one material selected from the group consisting of chloride ions and compounds containing chloride ions.

7. A method in accordance with claim 6 wherein the sodium and potassium are present in an amount between about 0.1 and 50 wt. %, expressed in terms of the metal based on the total weight of the contact material.

8. A method in accordance with claim 6 wherein the chloride ion is present in an amount between about 0.5 and 20 wt. %, expressed in terms of chlorine based on the total weight of the contact material.

9. A method in accordance with claim 6 wherein the sodium and potassium are present in an amount between about 0.1 and 50 wt. %, expressed in terms of the metal based on the total weight of the contact material, and the chloride ions are present in amounts between about 0.5 and 20 wt. %, expressed in terms of chlorine based on the total weight of the contact material.

10. A method for the conversion of methane to higher hydrocarbons, comprising:
    contacting a methane-containing gas and a free oxygen-containing gas with a solid contact material selected from the group consisting of:
    (a) a solid contact material consisting essentially of: (1) at least one oxide of at least one metal selected from the group consisting of Group IA metals, and (2) at least one oxide of at least one metal selected from the group consisting of calcium, strontium and barium; and
    (b) a solid contact material consisting essentially of: (1) at least one oxide of at least one metal selected from the group consisting of Group IA metals, (2) at least one oxide of at least one metal selected from the group consisting of calcium, strontium and barium and (3) at least material selected from the group consisting of chloride ions and compounds containing chloride ions,
    under conditions sufficient to convert said methane to a significant amount of higher hydrocarbons.

11. A method in accordance with claim 10 wherein the methane-containing gas is natural gas.

12. A method in accordance with claim 10 wherein the free oxygen-containing gas is air.

13. A method in accordance with claim 10 wherein the free oxygen-containing gas is oxygen.

14. A method in accordance with claim 10 wherein a diluent gas is present.

15. A method in accordance with claim 10 wherein the volumetric ratio of methane to free oxygen is at least about 1/1.

16. A method in accordance with claim 10 wherein the volumetric ratio of methane to free oxygen is between about 1/1 and 30/1.

17. A method in accordance with claim 10 wherein the temperature of contacting is at least about 500° C.

18. A method in accordance with claim 10 wherein the solid contact material consists essentially of: (1) at least one oxide of at least one metal selected from the group consisting of Group IA metals, and (2) at least one oxide of at least one metal selected from the group consisting of calcium, strontium and barium.

19. A method in accordance with claim 18 wherein the Group IA metal is present in an amount between about 0.1 and 50 wt. %, expressed in terms of the metal based on the total weight of the contact material.

20. A method in accordance with claim 10 wherein the solid contact material consists essentially of: (1) at least one oxide of at least one metal selected from the group consisting of Group IA metals, (2) at least one oxide of at least one metal selected from the group consisting of calcium, strontium and barium and (3) at least one material selected from the group consisting of chloride ions and compounds containing chloride ions.

21. A method in accordance with claim 20 wherein the Group IA metals are present in an amount between about 0.1 and 50 wt. %, expressed in terms of the metal based on the total weight of the contact material.

22. A method in accordance with claim 20 wherein the chloride ions are present in an amount between about 0.5 and 20 wt. %, expressed in terms of expressed in terms of chlorine based on the total weight of the contact material.

23. A method in accordance with claim 20 wherein the Group IA metals are present in an amount between about 0.1 and 50 wt. %, expressed in terms of the metal based on the total weight of the solid contact material, and the chloride ions are present in an amount between about 0.5 and 20 wt. %, expressed in terms of chlorine based on the total weight of the contact material.

24. A method in accordance with claim 10 wherein said contacting is carried out at a temperature in the range of about 500° C. to about 1500° C.

25. A method in accordance with claim 1 wherein the methane-containing gas is natural gas.

26. A method in accordance with claim 1 wherein the free oxygen-containing as is air.

27. A method in accordance with claim 1 wherein the free oxygen-containing gas is oxygen.

28. A method in accordance with claim 1 wherein a diluent gas is present.

29. A method in accordance with claim 1 wherein the volumetric ratio of methane to free oxygen is at least about 1/1.

30. A method in accordance with claim 1 wherein the volumetric ratio of methane to free oxygen is between about 1/1 and 30/1.

31. A method in accordance with claim 1 wherein the temperature of contacting is at least about 500° C.

32. A method in accordance with claim 1 wherein said contacting is carried out at a temperature in the range of about 500° C. to about 1500° C.

* * * * *